(12) United States Patent
McFall et al.

(10) Patent No.: US 6,702,796 B2
(45) Date of Patent: Mar. 9, 2004

(54) ABSORBENT INTERLABIAL DEVICE HAVING AN IMPROVED TAB

(75) Inventors: Ronald Ray McFall, West Chester, OH (US); Richard George Coe, Cincinnati, OH (US); Julie Michelle Lohre, Villa Hills, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 12 days.

(21) Appl. No.: 09/817,857

(22) Filed: Mar. 26, 2001

(65) Prior Publication Data

US 2002/0138057 A1 Sep. 26, 2002

(51) Int. Cl.$^7$ .................................................. A61F 13/15
(52) U.S. Cl. ............................................... 604/385.17
(58) Field of Search ........................ 604/385.01, 385.17

(56) References Cited

U.S. PATENT DOCUMENTS

| | | |
|---|---|---|
| 2,092,346 A | 9/1937 | Arone |
| 2,331,355 A | 10/1943 | Strongson |
| 2,629,381 A | 2/1953 | Brown |
| 2,662,527 A | 12/1953 | Jacks |
| RE24,137 E | 4/1956 | Jacks |
| 2,864,362 A | 12/1958 | Hermanson |
| 2,917,049 A | 12/1959 | Delaney |
| 3,183,909 A | 5/1965 | Roehr |
| 3,690,321 A | 9/1972 | Hirschman |
| 3,726,277 A | 4/1973 | Hirschman |
| 3,857,394 A | 12/1974 | Alemany |
| 3,905,372 A | 9/1975 | Denkinger |
| 3,983,873 A | 10/1976 | Hirschman |
| 4,046,147 A | 9/1977 | Berg |
| 4,095,542 A | 6/1978 | Hirschman |
| 4,142,476 A | 3/1979 | Hirschman |
| 4,175,561 A | 11/1979 | Hirschman |
| 4,196,562 A | 4/1980 | Hirschman |
| 4,260,570 A | 4/1981 | Ravel |
| 4,595,392 A | 6/1986 | Johnson et al. |
| 4,627,848 A | 12/1986 | Lassen et al. |
| 4,631,062 A | 12/1986 | Lassen et al. |
| 4,673,403 A | 6/1987 | Lassen et al. |
| 4,925,453 A | 5/1990 | Kannankeril |
| 4,946,454 A | 8/1990 | Schmidt |
| 5,057,096 A | 10/1991 | Faglione |
| 5,074,855 A | 12/1991 | Rosenbluth et al. |

(List continued on next page.)

FOREIGN PATENT DOCUMENTS

| | | |
|---|---|---|
| DE | 4032119 A1 | 4/1992 |
| EP | 0161663 A1 | 11/1985 |
| EP | 0 162 451 A1 | 11/1985 |
| FR | 2 420 339 | 10/1979 |
| GB | 588689 | 5/1947 |
| GB | 754481 | 8/1956 |
| JP | 3023887 | 1/1991 |
| JP | 09-099009 | 4/1997 |
| WO | WO 96/07379 A1 | 3/1996 |
| WO | WO 98/08475 A1 | 3/1998 |

*Primary Examiner*—Weilun Lo
*Assistant Examiner*—Catharine Anderson
(74) *Attorney, Agent, or Firm*—Matthew P. Fitzpatrick; Ingrid N. Hickman; Roddy M. Bullock

(57) ABSTRACT

Absorbent interlabial devices are disclosed. Preferably, the absorbent interlabial device has a liquid pervious topseet, a liquid impervious backsheet, and an absorbent core disposed between the topsheet and the backsheet. The device preferably also has a grasping tab joined to the backsheet. The tab preferably has at least a first zone and a second zone where the stiffness of the first zone is greater than the stiffness of the second zone. Preferably, the tab is made up of multiple layers. These layers are preferably laminated to each other in the first zone and are not laminated to each other in the second zone.

13 Claims, 4 Drawing Sheets

U.S. PATENT DOCUMENTS

| | | |
|---|---|---|
| 5,169,394 A | 12/1992 | Jean |
| 5,230,119 A | 7/1993 | Woods et al. |
| 5,290,262 A | 3/1994 | Vukos et al. |
| 5,336,208 A | 8/1994 | Rosenbluth et al. |
| 5,484,429 A | 1/1996 | Vukos et al. |
| 5,558,656 A | 9/1996 | Bergman |
| H1614 H | 11/1996 | Mayer et al. |
| 5,573,523 A | 11/1996 | Whalen et al. |
| H1634 H | 2/1997 | Oetjen et al. |
| D380,261 S | 6/1997 | Ely |
| 5,672,165 A | 9/1997 | Belecky et al. |
| 5,702,380 A | 12/1997 | Walker |
| 5,762,644 A | 6/1998 | Osborn, III et al. |
| 5,771,524 A | 6/1998 | Woods et al. |
| 5,853,401 A | 12/1998 | Mayer et al. |
| 5,885,265 A | 3/1999 | Osborn, III et al. |
| 5,891,126 A | 4/1999 | Osborn, III et al. |
| 5,895,381 A | 4/1999 | Osborn, III |
| 5,916,205 A | 6/1999 | Olson et al. |
| 5,928,452 A | 7/1999 | McFall et al. |
| 5,964,689 A | 10/1999 | McFall et al. |
| 5,968,026 A | 10/1999 | Osborn, III et al. |
| 6,033,391 A | 3/2000 | Osborn, III et al. |
| 6,044,515 A | 4/2000 | Zygmont |
| 6,045,544 A | 4/2000 | Hershberger et al. |
| 6,123,693 A | 9/2000 | Osborn, III |
| 6,131,736 A | 10/2000 | Farris et al. |
| 6,152,905 A | 11/2000 | Osborn, III et al. |
| 6,171,292 B1 | 1/2001 | Osborn, III et al. |
| 6,183,456 B1 | 2/2001 | Brown et al. |
| 6,270,486 B1 | 8/2001 | Brown et al. |
| 6,350,258 B1 * | 2/2002 | Markowiecki ........... 273/138.1 |

* cited by examiner

ABSORBENT INTERLABIAL DEVICE HAVING AN IMPROVED TAB

FIELD OF THE INVENTION

This invention relates to absorbent devices, and more particularly to an improved absorbent device that is worn interlabially by female wearers for catamenial purposes, incontinence protection, or both.

BACKGROUND OF THE INVENTION

All manner and variety of absorbent articles configured for the absorption of body fluids such as menses, urine and feces are well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage (if inserted properly). Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. Nos. 5,074,855 and 5,336,208 issued to Rosenbluth, et al. on Dec. 24, 1991 and Aug. 9, 1994 respectively, and U.S. Pat. No. 5,484,429 issued to Vukos, et al. on Jan. 16, 1996. A commercially available interlabial device is the IN-SYNC miniform interlabial pad which is marketed by A-Fem of Portland, OR and described in U.S. Pat. Nos. 3,983,873 and 4,175,561 issued to Hirschman on Oct. 5, 1976 and Nov. 27, 1979, respectively.

Many of these devices have not met with great commercial success, however. There are drawbacks associated with all of the above products. For example, the device described in the Delaney patent does not appear to be capable of an easy and comfortable insertion, due to the possibility of the layers of absorbent material opening up during insertion. The commercially available IN-SYNC interlabial device suffers from the disadvantage that many consumers find it difficult to insert properly and may cause some consumers discomfort especially if not properly inserted. Even when such a device is properly inserted, it may tend to allow by-pass flow around its edges. Such flow can cause body soiling or panty soiling which many consumers find unacceptable. Additionally, previously known interlabial devices such as the IN-SYNC miniform may not reliably cover the urethra and/or the vaginal introitus during all body movements (e.g. when the wearer is squatting). Such products may also not be reliably expelled when the wearer urinates.

Another factor affecting the success of the device is the ease of use, particularly with respect to the insertion and removal of the device. Typically, the user grasps the device with her fingers and inserts it in position. The user may also need to grasp the device for removal, particularly if it is not expelled during urination. For both insertion and removal, it is desirable that the user not touch the body-facing portion of the device. Thus, for ease of insertion and/or removal, a grasping tab or other gripping surface is very beneficial. Published Application WO 99/56689 (which is a co-pending and commonly assigned application designating the United States) describes an absorbent interlabial device provided with a grasping tab in which the grasping tab is an integrally formed extension of the backsheet of the device. While such integrally formed grasping tabs are acceptable and are easy to manufacture, even further opportunities for improvements in the overall performance and acceptance of the device are available.

For example, it has been found during development of the present invention that it is desirable to provide a grasping tab which is relatively stiff along at least some of its height. This serves to transmit the forces of insertion to the device and reduces the tendency of the tab to simply collapse upon itself. Stiffness of the grasping tab, however, can lead to discomfort associated with wearing of the device if this stiffness is uniform throughout the extent of the tab. Therefore, the present invention provides an interlabial device with an improved grasping tab having two or more zones which are tailored to act in combination to provide both insertion and removal success as well as a superior using experience.

SUMMARY OF THE INVENTION

This invention relates to absorbent devices, and more particularly to an improved absorbent device that is insertable into the interlabial space of a female wearer for catamenial purposes, incontinence protection, or both.

The absorbent interlabial device of the present invention comprises a backsheet and a tab joined to the backsheet and depending therefrom. The tab comprises a first zone and a second zone. The first zone of the tab has a first stiffness and the second zone has a second stiffness. The first stiffness is greater than the second stiffness.

Preferably, the first zone is located distal to the location of joining between the backsheet and the tab and the second zone is located proximal to the location of joining between the backsheet and said tab. The tab is preferably comprised of multiple layers. Such multiple layers may preferably be laminated to one another in the first zone and are not be laminated to one another in the second zone. Such selective lamination and lack of lamination allows one or more of the multiple layers to move independently with respect to another of the multiple layers in at least a portion of the second zone.

In some embodiments, the tab comprises three layers of material. All of the three layers may be laminated to one another in the first zone and wherein all of the three layers may be free to move independently with respect to one another in at least a portion of the second zone. In a variation, the tab may have a first outer layer and a second outer layer and an inner layer positioned between the first and the second outer layers, wherein the first outer layer and the second outer layer of the tab are independently joined to the backsheet of the absorbent device. Preferably, the first and second outer layers of the tab are joined to the backsheet of the device on either side of the longitudinal centerline.

In some embodiments, the tab comprises three layers of material including a first outer layer, a second outer layer, and a middle layer. The first outer layer may be laminated to the middle layer, and the second outer layer may be laminated to the middle layer in the first zone. In the second zone, the second outer layer may be not laminated to another layer thereby allowing the second layer to move independently with respect to the other layers. Preferably, the first and second outer layers of the tab are joined to the backsheet of the device on either side of the longitudinal centerline.

In some embodiments, the first zone of the tab comprises three layers of material including a first outer layer, a second outer layer, and a middle layer. The first outer layer is laminated to the middle layer, and the second outer layer is laminated to the middle layer. The second zone of the tab comprises two layers including the first outer layer and the second outer layer. The first outer layer and the second outer layer are not laminated to another layer in the second zone. Preferably, the first and second outer layers of the tab are joined to the backsheet of the device on either side of the longitudinal centerline.

In some embodiments, the tab comprises two layers. In the first zone, the two layers are laminated to each other. In the second zone the two layers are not laminated to each other. Preferably, the two layers of the tab are joined to the backsheet of the device on either side of the longitudinal centerline.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
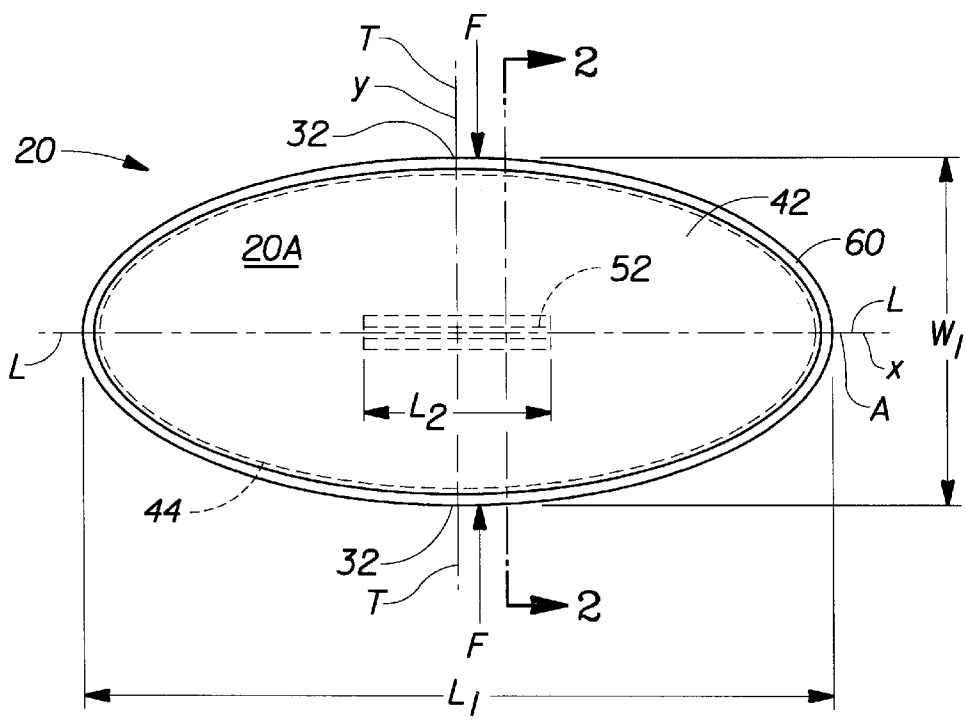
FIG. 1 is a top plan view of the absorbent interlabial device of the present invention.
Figure 2:
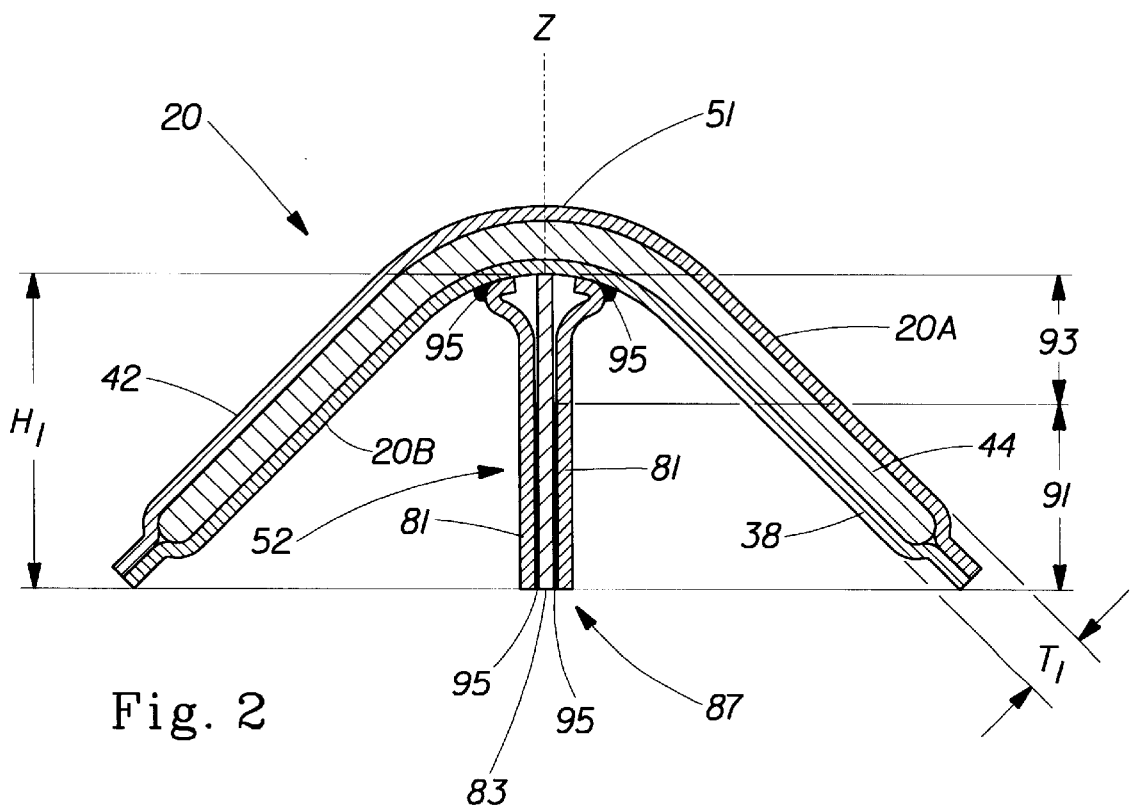
FIG. 2 is a cross sectional view of the absorbent interlabial device of the present invention, taken along line 2—2 of FIG. 1.
Figure 3:
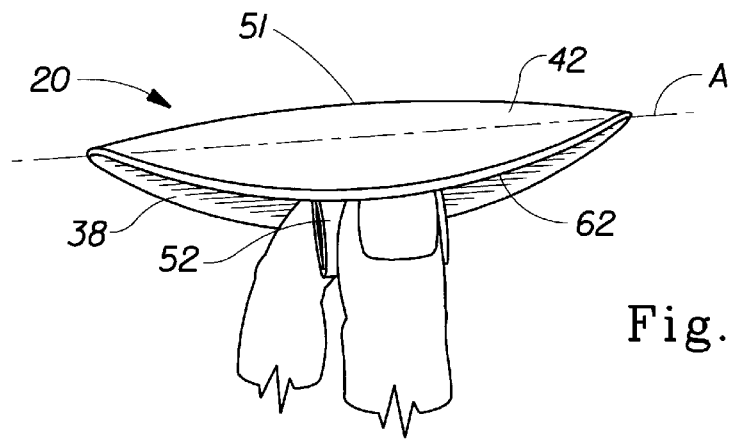
FIG. 3 shows the absorbent interlabial device of the present invention folded along the axis of preferred bending and being grasped for insertion by the wearer's fingers.

The present invention is directed to an absorbent interlabial device. FIGS. 1–3 shows one embodiment of an absorbent interlabial device, interlabial device 20. The present invention, however, is not limited to a structure having the particular configuration shown in the drawings.

As used herein the term "absorbent interlabial device" refers to a structure which has at least some absorbent components, and which is specifically configured to reside within the interlabial space of a female wearer during use. When the absorbent interlabial device 20 is properly sized for an individual wearer, more than half of the entire absorbent interlabial device 20 of the present invention resides within such interlabial space. Preferably substantially the entire absorbent interlabial device 20 resides within such interlabial space, and preferably the entire absorbent interlabial device 20 may reside within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The absorbent interlabial device 20 shown in FIG. 1 has a longitudinal centerline L which runs along the "x" axis. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line axis or direction that is generally perpendicular to the longitudinal direction. The lateral direction is shown in FIG. 1 as the "y" direction. The absorbent interlabial device 20 shown in FIG. 1 also has a transverse centerline T. The "z" direction, shown in FIG. 2, is a direction parallel to the vertical plane described above. The term "upper" refers to an orientation in the z-direction toward the wearer's head. "Lower" or downwardly is toward the wearer's feet.

The interlabial device 20 shown in FIGS. 1–3 is in one preferred configuration. The interlabial device 20 has a body-facing (or "body-contacting" side) 20A and an opposed underside 20B. The interlabial device comprises a pad-like main body portion (or "central absorbent portion") 22 and a placement and removal tab 52 (referred to as a "grasping tab" or "tab") which is joined to the backsheet 38. The overall interlabial device can have a "T"-shaped cross-sectional configuration. Additionally, the overall interlabial device 20 may have a ridge or crease 51 formed in the body facing surface 20A by virtue of the manner of attachment of the tab 52 to the backsheet 38. Such a ridge 51 is beneficial as will be discussed further below, but is not necessary.

The main body portion 22 can be in any suitable configuration. Non-limiting examples of shapes for the main body portion 22 when viewed from the top as in FIG. 1 include ovoid, elliptical, trapezoidal, rectangular, triangular, diamond-shaped, or any combination of the above. As shown in FIG. 1, the preferred plan view shape for the main body portion 22 and overall absorbent interlabial device 20 is generally ovoid or elliptical. The plan view shape of the main body portion 22 tapers from the transverse centerline T towards its front and rear ends.

As shown in FIGS. 1–2, the interlabial device may comprise a liquid pervious topsheet 42, a liquid impervious backsheet 38 joined to the topsheet 42, and an absorbent core 44 positioned between the topsheet 42 and the backsheet 38. A grasping tab 52 is joined to the garment facing side of the backsheet 38 and depends downwardly there from. The interlabial device 20 should be of a suitable size and shape that allows at least the majority of the device 20 to fit comfortably within the wearer's interlabial space and to cover the wearer's vaginal orifice, and preferably also the wearer's urethra. The interlabial device 20 preferably at least partially blocks, and more preferably completely blocks and intercepts the flow of menses, urine, and other bodily exudates from the wearer's vaginal orifice and urethra.

The size of the interlabial device 20 is important to its comfort and effectiveness. The length of the absorbent interlabial device 20 is measured along the longitudinal centerline L in the longitudinal direction (or "x"-direction). The absorbent interlabial device 20 preferably has a length $L_1$ which is greater than about 60 mm and less than about 130 mm. More preferably, the device might be offered in a variety of lengths where such length $L_1$ is about 80 mm, about 90 mm and about 110 mm for different sizes (such as a Lite, a Medium, and a Long product). The width of the interlabial device 20 is measured along the transverse centerline T in the transverse direction (or "y"-direction). The absorbent interlabial device 20 preferably has a width $W_1$ which is between about 30 mm and about 60 mm. Preferably, the width $W_1$ is about 50 mm. The thickness (or caliper) is the "z"-direction dimension of the device 20. Caliper measurements given herein were measured using an AMES gage with a 0.25 psi (1.7 kPa) (gauge) load and a 0.96 inch (2.44 cm) diameter foot. Those skilled in the art will recognize that if a 0.96 inch (2.44 cm) diameter foot is not appropriate for a particular sample size, the foot size may be varied while the load on the gauge is accordingly varied to maintain a confining pressure of 0.25 psi (1.7 kPa) (gauge). The caliper $T_1$ of the absorbent interlabial device 20 is less than the width $W_1$ and the length $L_1$ of the device 20. Preferably the caliper $T_1$ of the absorbent interlabial device 20 is less than or equal to about 8 mm, more preferably the caliper $T_1$ is less than about 6 mm, and even more preferably less than about 4 mm.

Construction of the absorbent interlabial device 20 according to the particular size parameters given above results in a product with increased comfort and effectiveness compared to previous interlabial devices. For example, many women find interlabial pads which are shorter than the absorbent interlabial device 20 of the present invention (such as previous interlabial pads) to be difficult to position properly within the interlabial space. Even if such pads are positioned properly they have an increased tendency to allow by-pass flow of body exudates around the edges of the pad. Additionally, previous pads were not equipped with a liquid impervious backsheet. These pads, therefore could allow body and panty soiling as a result of contact with the bottom surface of the pad. Larger pads (such as sanitary napkins configured for partial interlabial disposition) have a tendency to move to an unacceptable degree as the wearer moves. Therefore, the close contact of such pads with the interlabial tissues may serve as a drawback rather than an advantage. The present device, by contrast, maintains good contact with the interlabial tissues, but does not have a significant portion of the device contacting the remainder of the body, the undergarments, or other locations where unnecessary movement and corresponding discomfort can occur.

The interlabial device 20 is preferably provided with sufficient absorbency to absorb and retain the exudates discharged from the wearer's body. The capacity of the product, however, is dependent at least partially upon the physical volume of the absorbent interlabial device 20. The absorbent interlabial device preferably has a capacity of at least about 1 g of 0.9% by weight saline solution, and may have a capacity of up to about 30 g by using absorbent gels or foams that expand when wet. Capacities may typically range from about 2 to about 10 grams, for saline. Preferably, the capacity of the device 20 is greater than about 6 g for saline. Those skilled in the art will recognize that the capacity for absorption of body exudates such as menses will typically be smaller than the capacities given above for absorption of saline. A method for measuring absorbent capacity is described in the Test Methods section, below. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The individual components which may be suitable for the various embodiments of the sanitary napkin 20 of the present invention will now be looked at in greater detail with reference to FIGS. 1–3.

The topsheet 42 comprises a first liquid pervious component. The topsheet 42 should be compliant, soft feeling, and non-irritating to the wearer's skin. Further, the topsheet 42 is liquid pervious permitting liquids (e.g., menses and/or urine) to readily penetrate through its thickness. A suitable topsheet 42 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers.

One suitable topsheet 42 for use in the present invention is a nonwoven material formed of starch bonded rayon fibers. The material is similar to those used as an overwrap for tampons (in particular TAMPAX tampons). Generally, materials which are known in the art as suitable for use as a tampon overwrap are also suitable for use as a topsheet 42 in the present invention. The topsheet 42 preferably may have a basis weight of about 15 g/m² and may be obtained from BBA Nonwovens of Green Bay, Wis. This material is particularly suitable for use as a topsheet 42 because it is a biodegradable material. Other preferred topsheets may include a latex bonded rayon material (with both 3 and 1.5 Denier fibers being acceptable) available from PGI of Bensen, N.C. Other suitable topsheets for use in the interlabial device 20 of the present invention are described in U.S. application Ser. No. 09/637,440 filed on Aug. 11, 2000.

As used herein, the term "biodegradable materials" refers to a material having greater than or equal to about 70% biodegradation (percentage of theoretical carbon dioxide evolution) after 28 days when measured according to the Sturm Test which has been designated Method 301B by the Organization for Economic Cooperation and Development, 2 rue Andre Pascal, 75775 Paris Cedex 16, France. Preferably, the materials comprising the present invention have a biodegradation of greater than about 80% and, more preferably, biodegradation is greater than or equal to about 90%.

Another suitable type of topsheet 42 may comprise an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; U.S. Pat. No. 4,637,819 entitled "Macroscopically Expanded Three-Dimensional Polymeric Web for Transmitting Both Dynamically Deposited and Statically Contacted Fluids From One Surface to the Other," which issued to Ouellette, et al. on Jan. 20, 1987; U.S. Pat. Nos. 4,609,518 and 4,629,643 both issued to Curro, et al. on Sep. 2, 1986 and Dec. 16, 1986, respectively; U.S. Pat. No. 5,006,394 "Multilayer Polymeric Film" issued to Baird on Apr. 9, 1991; and U.S. patent application Ser. No. 08/442,935 entitled "Fluid Transport Webs Exhibiting Surface Energy Gradients" filed in the name of Ouellette, et al. on May 31, 1995 (PCT Publication WO 96/00584, published Jan. 11, 1996). A preferred formed film topsheet for the present invention is the formed film described in one or more of the above patents and marketed on sanitary napkins by The Procter & Gamble Company of Cincinnati, Ohio as the "DRI-WEAVE" topsheet.

In embodiments in which the topsheet is an apertured film, the body surface of the apertured film topsheet is preferably hydrophilic to help liquids transfer through the topsheet 42 faster than if the body surface was not hydrophilic so as to diminish the likelihood that menstrual fluid will flow off the topsheet 42 rather than flowing into and being absorbed by the absorbent core 44. The body surface of the topsheet 42 can be made hydrophilic by treating it with a surfactant such as is described in U.S. Pat. No. 4,950,254 issued to Osborn, III. In a preferred embodiment, surfactant is incorporated into the polymeric materials of the formed film topsheet.

The inner surface of topsheet 42 may be secured in contacting relation with an underlying absorbent layer. This contacting relationship results in liquid penetrating topsheet 42 faster. The topsheet 42 may be kept in a contacting relationship with an underlying layer by bonding the topsheet 42 to the underlying layer. However, it is not absolutely necessary to bond the face of the topsheet 42 to the face of the underlying layer. The topsheet 42 can be maintained in contact with an underlying absorbent component, by entangling the fibers of the underlying layer with the topsheet, by fusing the topsheet 42 to an underlying absorbent layer by a plurality of discrete individual fusion bonds, or by any means known in the art. The topsheet can also be maintained in contact with the underlying absorbent material due to the application of the pressure of the body against the body-contacting surface 20A of the interlabial device 20.

It is not necessary that the topsheet 42 comprise a layer or material which is separate or distinct from the absorbent core 44. The topsheet 42 and absorbent core 44 may consist of one unitary structure in which the body-contacting surface of the absorbent core 44 will serve as the liquid pervious topsheet 42. In such an embodiment, the liquid pervious body contacting surface may be hydrophilic or treated so as to render it hydrophilic such that fluids readily penetrate through the surface and into the interior of the absorbent core 44. Additionally, the unitary topsheet 42 and absorbent core 44 may be provided with a pore size, capillary, or hydrophilicity gradient to assist in the absorption and retention of fluids in the interior of the absorbent core 44.

The absorbent core 44, which is best seen in FIG. 2, is positioned between the topsheet 42 and the backsheet 38. The absorbent core 44 provides the means for absorbing exudates such as menses and other body fluids. The absorbent core 44 preferably is generally compressible, conformable, and non-irritating to the user's skin. Preferably, the absorbent core 44 has the same general shape as the overall absorbent interlabial device 20.

The absorbent core 44 may comprise any suitable material that is capable of absorbing and/or retaining liquids (e.g. menses and/or urine). The absorbent core 44 be manufactured from a wide variety of liquid-absorbent materials commonly used in absorbent articles such as comminuted wood pulp which is generally referred to as airfelt. Examples of other suitable absorbent materials include cotton fibers or cotton linters, creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers (in fibrous and particulate form); absorbent gelling materials; or any equivalent material or combinations of materials, or mixtures of these. Preferred absorbent materials comprise folded tissues, cotton batts, woven materials, nonwoven webs, rayon including needle punched rayon, and thin layers of foam. The absorbent core 44 may comprise a single material. Alternatively, the absorbent core 44 may comprise a combination of materials.

A particularly preferred material for the absorbent core 44 is batt of rayon or a rayon/cotton blend. A tri-lobed rayon known as GALAXY rayon available from Acordis Fibers, Inc. of Axis, Ala. has been found to work well for the material comprising the absorbent core 44. Sarille L rayon (a conventional rayon structure—i.e. not tri-lobed) is also suitable and is available from Acordis Fibers. A 50%/50% blend of cotton combers (available from BBA Nonwovens of Griswoldville, Mass.) and Sarille L rayon (having a glycerin or leomin finish and obtained from Acordis Fibers) has been found to work well. Generally, absorbent materials which are suitable for use in tampons have been found to work well in the absorbent core 44 of the present device. Therefore, carded absorbent layered structures such as the 50/50 blend of cotton and rayon are suitable. The basis weight for the core 44 of the interlabial device 20 may be about 200 to about 500 g/m$^2$. Additionally, core materials and structures described in U.S. patent application Serial No. 09/637,440 filed on Aug. 11, 2000 are also suitable.

The backsheet 38, which is best shown in FIGS. 2 and 3, prevents the exudates absorbed and contained in the absorbent core 44 from wetting articles and/or body parts which may contact the absorbent interlabial device 20 such as pants, pajamas, undergarments, pubic hair, the wearer's thighs, etc. The backsheet 38 should be flexible and impervious to liquids (e.g., menses and/or urine).

The backsheet 38 is impervious to liquids (e.g., menses and/or urine) and is preferably flexible, As used herein, the term "flexible" refers to materials which are compliant and will readily conform to the general shape and contours of the human body. The backsheet 38 also provides protection for the wearer's fingers as the absorbent interlabial device 20 is inserted, or as the device is optionally removed with the fingers.

The backsheet 38 may comprise a woven or nonwoven material, polymeric films such as thermoplastic films of polyethylene or polypropylene, composite materials such as a film-coated nonwoven material, or organic material such as a collagen film. Other suitable materials include biodegradable polymers that can be made into films and the like. A Polybutylene succinate adipate film colored with Ampacet 110361 available as BIONELLE 3001 obtained Showa High Polymer Co. of Tokyo, Japan has been found to work well. Other suitable materials include Matter Bi ZF03U-A obtained from Bicorp Co., distributor for Novamont S.P.A. of Rome, Italy and Biopol biodegradable polymer obtained from Monsanto, and Nordenia biodegradable polyester based film obtained from M&W Verpackungen GmBH, Germany. In one embodiment, the backsheet may be made from a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. Preferably, however, the backsheet comprises a film having a similar thickness, but which is made from a biodegradable material, such as one of the biodegradable polymers described above (e.g. BIONELLE). Other suitable backsheet materials include Polyester Amide (BAK) available from Nordinia of Bronau, Germany.

The backsheet 38, may be made in any suitable color, such as white, pink, or lavender. In preferred executions of the present invention, the backsheet 38 color may be used to indicate a performance characteristic of the device. U.S. patent application Ser. No. 09/685,259 filed on Oct. 10, 2000 describes the use of such color signals in greater detail.

The backsheet may permit vapors to escape from the device 20 (i.e., be breathable) while still preventing exudates from passing through the backsheet. A suitable breathable backsheet material is a laminate of an apertured film such as that described in U.S. Pat. No. 3,929,135 issued to Thompson which is inverted so that the smaller openings of the tapered capillaries face the absorbent core 44 which is adhesively laminated to a microporos film such as that described in U.S. Pat. No. 4,777,073.

Preferably, the backsheet 38 is dispersible and/or dissolvable in water. Polyvinyl alcohol (including co-polymers of polyvinyl alcohol) has been found to be suitable as a material for a dissolvable backsheet 38. The polyvinyl alcohol may be coated with a tissue, with a wax or other hydrophobic coating to reduce the rate at which it dissolves in water. This allows the backsheet 38 to maintain its integrity during use, while retaining the ability to dissolve in water during disposal of the device 20.

The term "dispersible" as applied herein to an absorbent interlabial device or a component thereof refers to an article or material which will disperse into at least two fragments in mildly agitated water. Such a device will break into pieces in a conventional toilet and/or domestic plumbing system, and will ultimately be effectively processed though a sewage treatment system. The term "dissolvable" as applied herein to an absorbent interlabial device or a component thereof refers to an article or material which will at least partially dissolve and essentially assume liquid form or otherwise be indistinguishable to the naked eye from the liquid medium in which it is dissolved.

The absorbent interlabial device 20 is preferably provided with an grasping tab 52 (also sometimes referred to as a "keel") joined to the backsheet 38. Tab 52 should have sufficient dimensions to aid in insertion into the interlabial space of the user. By "sufficient dimensions" it is meant that tab 52 can be gripped between the fingers (especially between the forefinger and thumb) of the user while maintaining control of the device during insertion into the interlabial space. For example, tab 52 has a height $H_1$ sufficient to form a gripping surface for the user's fingers. In one embodiment, height $H_1$ is at least equal to distance $T_1$ as shown in FIG. 2 and discussed above. Height $H_1$ can be at least about 10 mm, and is more preferably at least about 15 mm. There is no theoretical upper limit on the maximum height of the tab 52, but it is believed that at heights greater than about 30 mm, the tab 52 interferes with the proper use of the device 20 as well as the user's comfort.

The dimension of the tab 52 as measured parallel to the longitudinal axis L (that is dimension $L_2$) also may be about 10 mm, and is more preferably at least about 15 mm. In the embodiment shown in FIGS. 1–3, the tab 52 length $L_2$ may be about 25 mm. The width of the tab 52 (that is the dimension parallel to the transverse axis T) will depend on the structure of the tab 52 to produce the zones of varying stiffness as described in greater detail below.

The tab 52 may be made of a variety of materials and need not be absorbent. In the embodiment shown in FIGS. 1–3, the tab 52 is formed of a laminate of three layers. As shown in FIG. 2, the tab 52 is comprised of two outer layers 81 which have a middle layer 83 sandwiched therebetween. The layers of the tab 52 may be formed of any suitable material. In the embodiment shown in FIGS. 1–3, the outer layers 81 of the tab 52 may be formed from a material which is similar to the that of the backsheet 38. Polypropylene films and the like are suitable for such outer layers 81. Preferably, the outer layers 81 are non absorbent so as to be resistant to soiling, but may be absorbent if desired. The outer layers 81 may be formed of the same material or may comprise different materials. The outer layers 81 may comprise a single sheet which is wrapped over at the distal end 87 of the tab 52. Alternatively, the outer layers 81 may comprise fully discrete layers. Fully discrete layers may be easier to manufacture at high speeds, but such a construction is not necessary.

The middle layer 83 shown in FIG. 2 is comprised of a nonwoven airlaid material. The middle layer 83 may be any suitable layer and is generally selected to provide some stiffness to the tab 52 as a whole. A basis weight of about 60 g/m² is suitable to provide an appropriate level of stiffness for insertion and removal of the device 20.

The tab 52 is provided with at least two zones of differing stiffness, such as first zone 91 and second zone 93. For clarity of discussion, the first zone 91 will be that which has a greater degree of stiffness with respect to the second zone 93. This convention will be used, regardless of the location of the zones within the device 20. Preferably, the first zone 91 (that is, the zone having increased stiffness) is located remote from the location of attachment of the tab 52 to the backsheet 38, but other locations (including proximate to the location of attachment) are also possible. Such a first zone may extend from the distal end 87 of the tab 52 to any suitable location along the height of the tab 52. If the overall height $H_2$ of the tab 52 is about 16 mm, such first zone, might have a height of about 9 mm.

The second zone 93, has a decreased level of stiffness relative to the first zone 91. Preferably, the second zone is located in an area which includes the location of attachment of the tab 52 to the backsheet 38. Preferably, the second zone 93 extends from the end of the first zone 91 to the backsheet 38 of the device 20. In the embodiment shown in FIG. 2, the overall height $H_1$ of the tab 52 may be about 16, the first zone may have a height of about 9 mm, and the second zone 93 may have a height of about 7 mm. The zones preferably, but need not, extend along the entire length of the tab 52. If they do not, the first zone 91 may be located toward the middle portion of the tab 52 with respect to length. Alternatively, the first zone 91 may be located toward either end of the tab 52 along its length.

In the embodiment shown in FIG. 2, the tab 52 comprises three layers, outer layers 81, and a middle layer 83. The three layers are laminated together (such as with a suitable adhesive 95) over the extent of the first zone 91. The layers of the tab 52, are left free to move with respect to one another (in other words, are not attached, or are "delaminated") over the extent of the second zone 93. The lack of adhesive 95 in the region of the second zone 93 is responsible for the decreased stiffness of such second zone. Additionally, the freedom of movement of each of the outer layers 81 is desirable. In preferred embodiments, such as shown in FIG. 2, the tab 52 has two or more locations of attachment of the tab 52 to the backsheet 38. For example, each of the outer layers 81 may be separately and independently joined to the backsheet 38 (such as with a suitable adhesive 95) on either side of the longitudinal centerline L of the device 20. Such separate and independent attachment allows for flexibility and movement of the tab 52 during use of the device 20 (so as not to interfere with product comfort). The increased stiffness of the first zone 91, correspondingly allows the forces of insertion to be translated to the device 20, but such stiffness is not present to interfere with comfort when the device is actually being worn. It should be pointed out, that even if the tab attachment adhesive is provided on the backsheet in a single application (such as a 1 mm wide line of glue down the longitudinal centerline L), such separate and independent attachment of the outer layers 81 is still possible.

Figure 4:
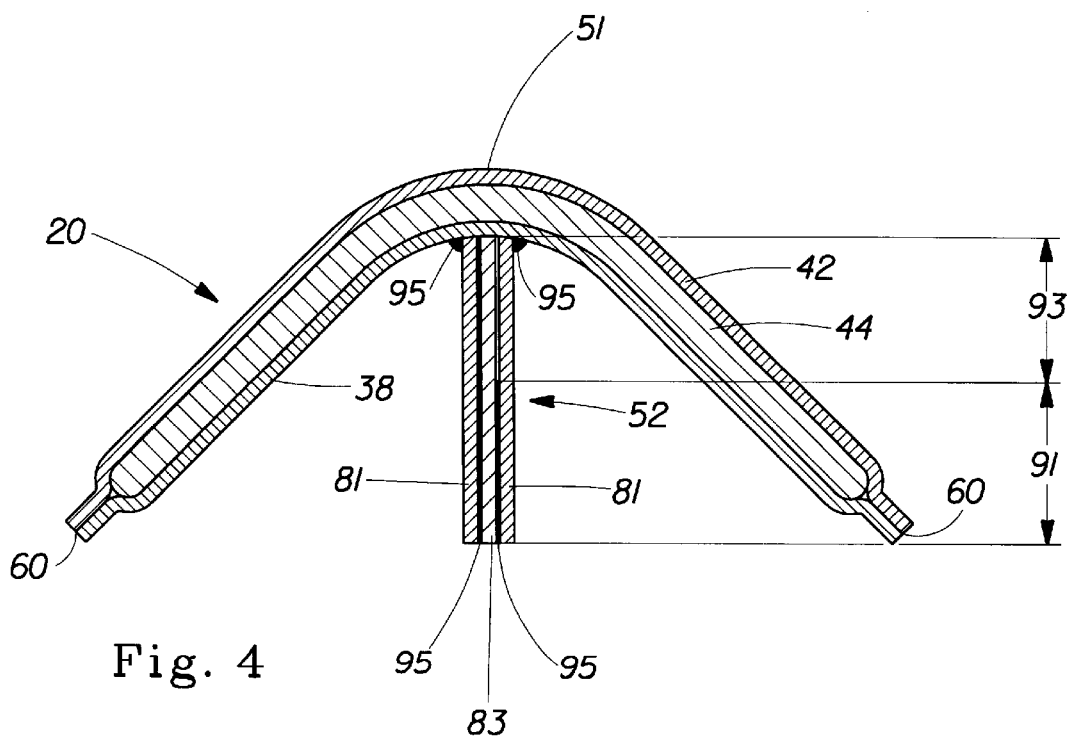
FIG. 4 is cross section view as in FIG. 2 showing an alternative embodiment of the tab.

Numerous variations of the tab 52 design described about are possible. For example, as shown in FIG. 4, the tab 52 may comprise three layers as described in FIG. 2. In the variation shown in FIG. 4, however, only one of the outer layers 81 is free to move with respect to the other two layers over the extent of the second zone 93. In other words, the "delamination" of the three layers in the second zone 93 is partial rather than complete as was the case in the embodiment shown in FIG. 2.

Figure 5:
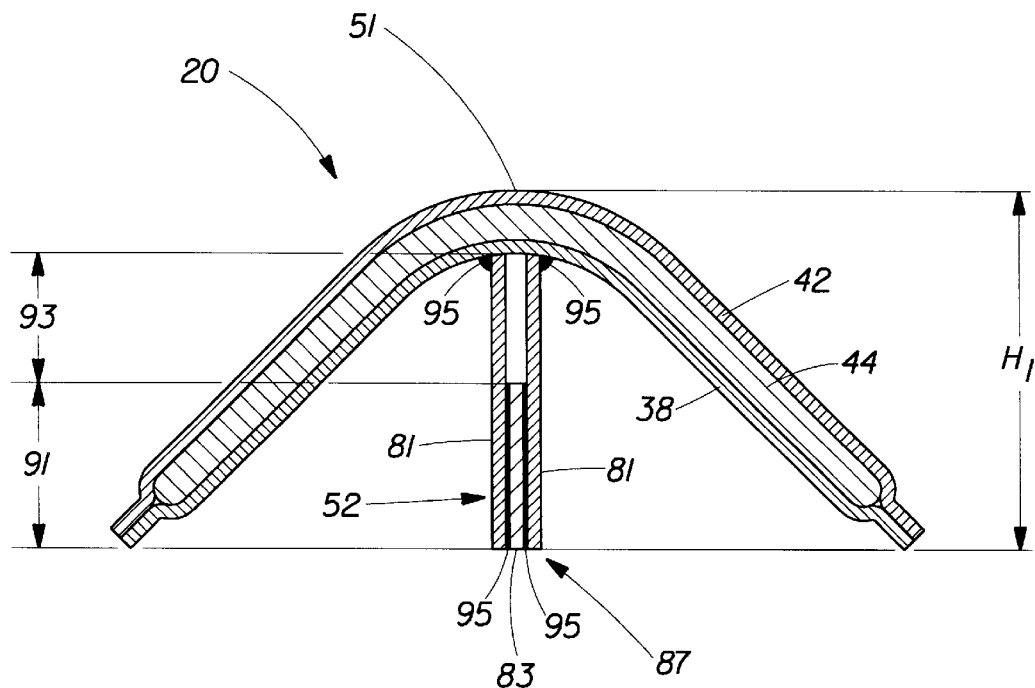
FIG. 5 is a cross section view as in FIG. 2 showing a second alternative embodiment of the tab.

FIG. 5 shows a variation in which the tab 52 is comprised of three layers, but in which the middle layer 83 extends only partially along the height $H_1$ of the tab 52. For example, the middle layer may only extend from the distal end 87 of the keel 52 until the end of the first zone 91. The three layers are laminated together within the first zone 91, but the remaining two layers are free to move with respect to one another in the second zone 93.

Figure 6:
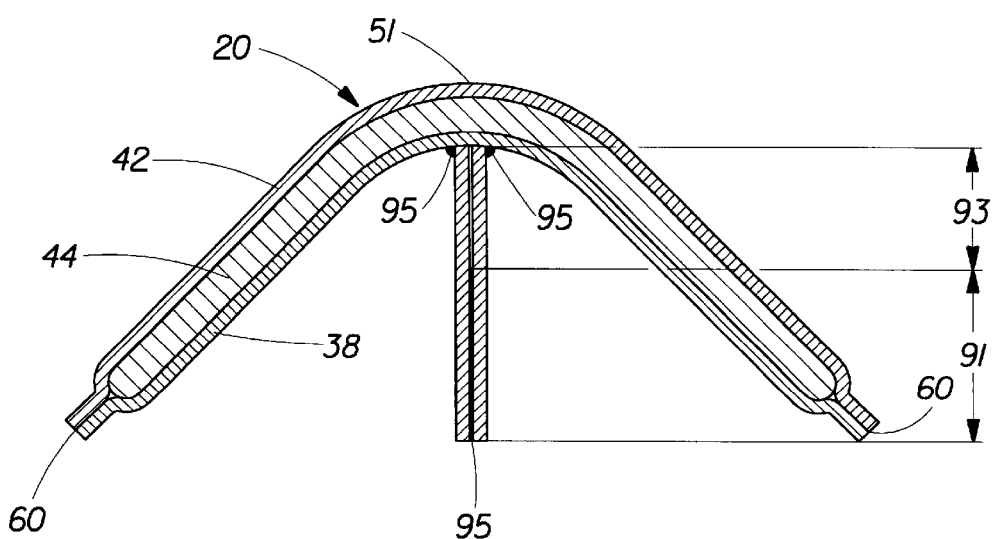
FIG. 6 is a cross section view as in FIG. 2 showing a third alternative embodiment of the tab.

FIG. 6 shows a variation in which the tab 52 comprises only two layers. These two layers (such as first layer 99 and second layer 101) may be laminated together (such as with adhesive 95) in the first zone 91. Such adhesive 95 lamination provides the increased stiffness property of the first zone 91. The two layers are left free to move with respect to one other in the second zone 93. In such an embodiment, the layers may comprise the same material, or may comprise different materials.

While the embodiments shown in FIGS. 2, and 4–6 show tabs 52 comprising multiple layer structures, such is not necessary in order to practice the present invention. The tab 52 of the present invention may comprise a single layer in which one portion (the first zone 91) has an increased stiffness relative to another portion (the second zone 93). Such increased stiffness of the first zone 91 may be provided by an agent which stiffness a portion of the tab 52 (such as adhesive). The increased stiffness may also be provided by varying the material properties of the tab 52, such as by using a naturally more stiff material in the first zone 91 or by using additional material in the fist zone 91.

As noted above, using a multiple layer structure for the tab 52 is not necessary. Such a multiple layer structure, however, provides the opportunity to add benefits beyond the zones of stiffness. For example, which two layers of the tab 52 are independently joined to the backsheet at either side of the longitudinal centerline L, the device 20 may be imparted with a ridge or crease 51 as a result of such attachment. As shown in FIG. 2, the tab 52 may be attached with adhesive 95 formed in two lines on either side of the longitudinal centerline L of the device 20. In such an example, each layer of the tab 52 may be spaced about 1 mm apart from each other. Such spacing may exceed 1 mm up to the width $W_1$ of the device 20. Preferably, however, the spacing of the layers is less than one-half of the width $W_1$ of the device 20. Such attachment starting at a location spaced from the longitudinal centerline, creates a crease 51 in the body facing surface 20A of the topsheet 42. This crease 51 is useful for product insertion and helps the labia to spread. The crease 51 also contributes to the formation of an axis of preferred bending, which is discussed in more detail below.

The tab 52 is preferably joined to the surface of the backsheet 38 which faces away from the topsheet 42. The tab 52 provides a location for the wearer to grasp the device 20 during insertion. The absorbent interlabial device 20 is designed to be expelled by urination. The tab 52, however, may provide an alternative mechanism for removal of the device 20 (i.e. removal with the fingers).

The components of the absorbent interlabial device 20 described above (topsheet 42, backsheet 38, absorbent core 44, and tab 52) can be assembled in any suitable manner. In the preferred embodiment shown in FIGS. 1–3, the components of the main body portion are assembled in a "sandwich" configuration with the components sized so that the edges of the topsheet 42 and backsheet 38 extend outward beyond the edges of the absorbent core 44. The topsheet 42 and backsheet 38 are preferably at least partially peripherally joined using known techniques. As shown in FIGS. 1 and 2, the topsheet 42 is preferably secured to backsheet 38 along a seam, such as seam 60. Seam 60 is preferably liquid impervious. The seam 60 can be formed by any means commonly used in the art for this purpose such as by gluing, crimping, or heat-sealing. The seam 60 and the area of the interlabial device 20 in the vicinity of the seam 60 should be soft, compressible, and conformable. If the seam 60 and surrounding area are too stiff or non-compressible, the wearer may experience discomfort when wearing the interlabial device 20.

The term "joined," as used herein, encompasses configurations in which an element is directly secured to another element by affixing the element directly to the other element; configurations in which the element in indirectly secured to the other element by affixing the element to intermediate member(s) which in turn are affixed to the other element; and configurations in which one element is integral with the another element, i.e., one element is essentially part of the other element.

The components of the absorbent interlabial device 20 can be joined together by adhesives, stitching, heat and/or pressure bonds, dynamic mechanical bonds, ultrasonic bonds, intermingling or entanglement of the fibers or other structural elements comprising the components of the absorbent interlabial device 20, such as by meltblowing the fibers comprising one component onto another component, extruding one component onto another, or by any other means known in the art. The components of the absorbent interlabial device 20 may be joined with water soluble adhesives in order to increase the tendency of the device 20 to disperse into a plurality of fragments in mildly agitated water (such as in a toilet). As discussed above, the tab 52 is preferably attached to the backsheet 38 in the manner discussed. Adhesives are suitable for this attachment, although other attachment mechanisms may be used as well.

Preferably, the interlabial absorbent device 20 of the present invention is toilet-disposable. The term "toilet-disposable" as used herein includes the following characteristics of an absorbent interlabial device: flushability, dispersibility, settleability, disintegrateability, and biodegradability. As used herein the terms "flushable" and "flushability" refer to a product's ability to pass though typically commercially available household toilets and plumbing drainage systems without causing clogging or similar problems that can be directly associated with the physical structure of the product.

"Settleability" refers to the tendency of an absorbent interlabial device, such as absorbent interlabial device 20 to eventually settle to the bottom of a septic tank or other sewage treatment system rather than to float on the surface of such tanks or sewage being processed. Preferably, the absorbent interlabial device 20 of the present invention is toilet-disposable and will disperse into at least two fragments within two hours of exposure to mildly agitated room temperature water.

Preferably, the absorbent interlabial device 20 comprises biodegradable materials. While biodegradable materials are preferred for the absorbent interlabial device 20, it is not necessary that each and every material used be biodegradable. For example, the device 20 may comprise superabsorbent particles which do not biodegrade, and this will not affect the ability of the overall device 20 to remain toilet-disposable and to be effectively processed in a sewage treatment system.

The absorbent interlabial device 20 of the present invention in its fully assembled configuration may comprise at least one axis of preferred bending A. The axis of preferred bending A is preferably located generally along the longitudinal centerline L of the absorbent interlabial device 20. The axis of preferred bending A is a line or axis along which the absorbent interlabial device 20 will tend to bend or fold when subjected to compressive forces F directed inwardly in the transverse direction at the sides 32 of the device 20. The axis of preferred bending A may result naturally from the product configuration, or the device 20 may be imparted with a weakened axis or region in any or all of the topsheet 42, backsheet 38 and core 44 to create the axis of preferred bending A. Such a weakened axis may be created by any variety of known techniques such as scoring, pre-folding, slitting, or the like. Additionally, if the preferred multiple layer tab 52 structure discussed above is used, the device may be imparted with a crease or ridge 51 which contributes to formation of such an axis of preferred bending. The absorbent interlabial device 20 may comprise a region of preferred bending made up of a plurality of axes of preferred bending. Any number of such axes may comprise such a region of preferred bending up to an infinite number.

The absorbent interlabial device 20 is folded along the axis of preferred bending A, as shown in FIG. 3, prior to insertion within the wearer's interlabial space. Once inserted, the device 20 will preferably tend to unfold slightly keeping the topsheet 42 of the device 20 in contact with the inner walls of the wearer's labia. The device 20 may be resiliently biased slightly along the axis of preferred bending A to increase the tendency of the device 20 to unfold. This allows the folded device 20 to act as a "spring" under both wet and dry conditions and, consequently, to increase the tendency of the topsheet 42 of the device to remain in contact with the inner surfaces of the labia when the absorbent interlabial device 20 is in place. A device 20 constructed according to the preferred embodiment described above, however, does not necessarily require any additional structural features to provide the ability to maintain such contact. The naturally moist surfaces of the labia will have a tendency to adhere to the material comprising the topsheet 42 further tending to keep the device 20 in contact with the inner surfaces of the labia.

The absorbent interlabial device 20 described herein is both flexible and compressible. Flexibility and compressibility are important to product comport. If the absorbent interlabial device 20 is too flexible, the device is not conveniently or easily placed between the folds of the labia, if it is too stiff, the device is uncomfortable and when the user is in a sitting position, the product can be forced forward against the clitoris causing discomfort.

The absorbent interlabial device 20 of the present invention is believed to offer several advantages over previous interlabial pads. The tab 52 of the present invention having zones of differing stiffness offer comfort and performance benefits during both insertion and in use. A minimum level of stiffness is desired in the tab 52 in order to get good insertion. Too much stiffness, however, will translate to the topsheet 42 of the device 20 and contribute to discomfort. The tab 52 described herein, however, allows for sufficient stiffness for insertion, which not causing comfort negatives by virtue of the less stiff second zone. Additionally, the independent attachment of the tab 52 to differing backsheet locations described in preferred embodiments allows the tab to move freely throughout 180° without distortion of the backsheet or remainder of the device.

Devices constructed with the size ranges and preferred shapes described above have been found to be particularly suited for reliable insertion by a variety of wearers. Additionally, the device 20 described above have been found to be particularly effective at catching clots which may be formed from menstrual discharges. This clot catching attribute is believed to be enhanced by the generally flat topsheet 42 of the device 20 which is folded along the axis of preferred bending A in use. The folded configuration of the device 20 when properly sized as described above allows for consistent coverage of the walls of the labia and the vaginal introitus. Such coverage substantially reduces the incidence of "by-pass" around the device 20 by menstrual or other bodily discharges which are exhibited by previous interlabial pads.

Superior performance in acquiring menstrual discharges, and clots in particular, is demonstrated by an absorbent interlabial device 20 of the present invention as described above in which the topsheet 42 and the absorbent core 44 comprise rayon.

The preferred shape of the absorbent interlabial device 20 shown in FIGS. 1–3 (i.e. one in which the device is tapered at the ends) allows the device to easily and comfortably fit the wearer's interlabial space. A device 20 with such a tapered shape, when folded along an axis of preferred bending A (as in FIG. 3) will have a profile in which highest point along the axis of bending A (as measured in the "z"-direction) is in the vicinity of the center of the device 20 rather than at the ends.

The liquid impervious backsheet 38 of the absorbent interlabial device 20 is also responsible for improved product performance. As described above, the backsheet reduces the likelihood of body or clothing soiling from discharges which are absorbed by the device 20. Additionally when the device 20 is folded along the axis of preferred bending A, the backsheet 38 will form a recess 62 which protects the wearer's fingers from soiling when the device 20 is inserted.

Previous interlabial pads have not combined the attributes of the device 20 of the present invention to obtain the performance and comfort results described herein. Several previous pads consisted of a small generally cylindrically shaped absorbent material which is inserted into the interlabial space. These devices were not provided with a liquid impervious backsheet. Consequently, they are characterized by a less cleanly insertion and removal and may be associated with increased panty and body soiling in comparison to the present device 20. Other previous pads did include an impervious backsheet, but the pads were much larger than the device 20 of the present invention and included significant portions which resided externally to the interlabial space. Such designs may also lead to increased body soiling as discharged bodily fluids migrate to the external surfaces of such pads. Additionally, the interlabial device 20 of the present invention is believed to offer comfort advantages (e.g. reduced wearing awareness) as compared to the above-described larger prior art pads.

It has been found during development of the present invention that the absorbent interlabial device 20 better conforms to the labial vault than previously available interlabial pads. Additionally, the generally flat and folded configuration of the absorbent interlabial device 20 of the present invention is found to give a better visual indication to users as to how to insert and use the device. Therefore, the device 20 of the present invention is associated with an easier and more accurate insertion as compared to previous interlabial pads.

As previously discussed, the absorbent interlabial device 20 of the present invention is designed to be placed within the interlabial space of a wearer. To use the absorbent interlabial device 20 of the present invention, the wearer grasps the tab 52 of the device 20. The device 20 is then further inserted by pushing with a finger or fingers in the recess 62 formed by the folded backsheet 38 while grasping the tab 52.

Figure 7:
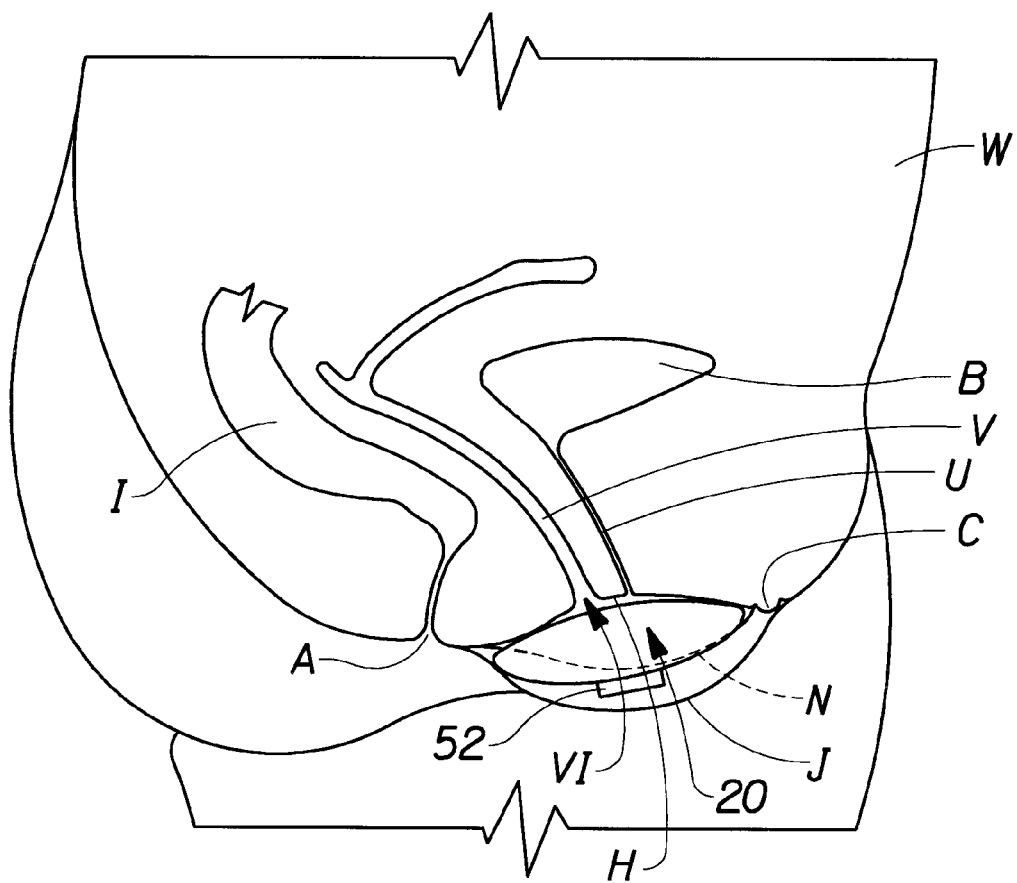
FIG. 7 is a cross-sectional saggital view of a human female wearer showing the placement of the absorbent interlabial device in the wearer's interlabial space.

As shown in FIG. 3, the folded device 20 forms a recess 62 within the folded backsheet 38 which covers the tips of the wearer's fingers during insertion. This feature provides for a hygienic insertion of the absorbent interlabial device 20 of the present invention. The wearer may assume a squatting position during insertion to assist in spreading the labial surfaces. FIG. 7 shows a preferred embodiment of the absorbent interlabial device 20 of the present invention inserted into the interlabial space of a wearer W. The urogenital members shown in FIG. 7 include the bladder B, the vagina V, the urethra U, the clitoris C, the large intestine I, the anus A, the vaginal introitus VI, the hymeneal ring H, the labia minora N, and the labia majora J. FIG. 7 shows the relationship of these anatomical features of the wearer W to the absorbent interlabial device 20 when the device is properly inserted for use. Once the absorbent interlabial device 20 is inserted, the topsheet 42 tends to adhere to the inside surfaces of the labia. When the wearer is standing, the labial walls close more tightly around the folded absorbent interlabial device 20.

The interlabial device 20 is preferably at least partially retained in place by exerting a slight laterally outwardly-oriented pressure on the inner surfaces of the wearer's labia minora, labia majora, or both. Additionally, the product may also be held by attraction of naturally moist labial surfaces to the material comprising the topsheet 42. Optionally, the interlabial device 20, or any suitable portion thereof, such as at least one body-contacting surface of the device can have a substance thereon to assist the device in staying in place in the desired position within the interlabial space. Preferably, such a substance should adhere the interlabial device 20 to the inside surfaces of the labia minora, or alternatively to the labia majora so that it remains adhered to these surfaces (on both sides of the interlabial space) unaided by the wearer's panties, or the like, when the wearer moves in a way that the labia spread (e.g., when the wearer is squatting with her feet about shoulder width apart). This will allow the device 20 to remain in place during wearing conditions, and will also insure that it is contacted by a stream of urine when the wearer urinates so that it will removed on urination or be easily dislodged by a wiping action, such as with toilet paper.

Typically, the unloaded device will weigh less than or equal to about 2 grams. The need for a substance to assist the interlabial device in staying in place becomes more important as the loading the interlabial device 20 is expected to hold (that is, the weight of absorbed bodily liquids) increases. Suitable substances, for such assistance are described in greater detail in Published Application WO 99/56689 (currently co-pending as U.S. Ser. No. 09/674, 473) and WO 99/56681 (co-pending as U.S. Ser. No. 09/266, 988).

The absorbent interlabial device 20 can be worn as a "stand alone" product. Additionally, superior performance in reducing body and clothing soiling over extended periods of wear time (such as overnight) can be obtained by using the absorbent interlabial device 20 as part of a "system" of feminine hygiene products. One such system which is effective in reducing soiling is an absorbent interlabial device, such as absorbent interlabial device 20, which is worn simultaneously with a sanitary napkin, or a pantiliner. Suitable systems (as well as kits embodying such systems) are described in greater detail in U.S. Pat. No. 6,183,456.

Numerous alternative embodiments of the absorbent interlabial device of the present invention are possible. For example, these products may also be used with emollients and/or medicinal treatments. For example, a suitable emollient for use on the absorbent interlabial device 20 of the present invention is comprised of about 65% petrolatum, about 28% Behenyl alcohol, and about 7% Beheneth-10. An emollient coating of about 0.03 g/pad has been found to be suitable. Other emollients such as those described in U.S. Pat. Nos. 6,183,456 and 5,891,126 are also suitable. The emollients, if used, may be applied in a continuous application or in an intermittent pattern. A patterns of stripped finish on the topsheet 42 is found to work well.

The absorbent interlabial device 20 of the present invention may be provided with a visual indication on the center of the topsheet 42 designating the area of greatest absorbent capacity of the device 20. Such an indication may consist of a differently colored region such as a pink oval. The indication may be about 12 mm wide and about 20 mm long. The absorbent interlabial device 20 may also be provided with a visual change indication. In other words, the device 20 may have a ring, bonding pattern, compression lines, or other visual indicator provided on the surface of the topsheet 42 at a predetermined distance inboard from the seam 60. When absorbed bodily discharges reach the visual change indication or outboard of the change indication, the user knows to replace the absorbent interlabial device 20. Such a change indication is particularly useful to users who remove the device 20 prior to urination and then re-insert the same device 20 if it has not yet reached its absorbent capacity.

If desired, the absorbent interlabial device 20 may be packaged in an individual package. Numerous types of packages are suitable such as those described in U.S. Pat. No. 6,183,456 or in U.S. patent application Ser. No. 09/695,544 filed on Oct. 24, 2000.

TEST METHODS

Absorbent Capacity

Absorbent capacity may be determined as follows. The test is performed on samples that have been conditioned by leaving them in a room at 50% relative humidity and at 73° F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and laid horizontally on a wire mesh screen having square openings 0.25 inches by 0.25 inches (0.64 cm by 0.64 cm) for five minutes to allow the saline to drain out to the article. Both sides of the article are then covered with absorbent blotters, such as the filter paper #631 available from the Filtration Science Corp., Eaton-Dikeman Division of Mount Holly Springs, Pa. A uniform 1 pound per square inch load is placed over the article to squeeze excess fluid out. The absorbent blotters are replaced every 30 seconds until the amount of fluid transferred to the absorbent blotters is less than 0.5 grams in a 30 second period. Next, the article is weighed to the nearest 0.1 gram and the dry weight of the article is subtracted. The difference in grams is the absorbent capacity of the article.

This concludes the test.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent device insertable into the interlabial space of a female wearer, said absorbent device having a length, a width, a thickness, and a longitudinal centerline, said absorbent device comprising a backsheet and a tab joined to said backsheet and depending therefrom; wherein said tab comprises a first zone and a second zone, said first zone being located remote from the location of joining between said backsheet and said tab; and said second zone being located proximal to the location of joining between said backsheet and said tab; and wherein said first zone has a first stiffness, said second zone has a second stiffness, said first stiffness being greater than said second stiffness.

2. The absorbent device of claim 1 wherein said tab is comprised of multiple layers.

3. The absorbent device of claim 2 wherein said multiple layers of said tab are laminated to one another in said first zone and wherein said layers of said tab are not laminated to one another in said second zone thereby allowing one or more of said multiple layers to move independently with respect to another of said multiple layers in at least a portion of said second zone.

4. The absorbent device of claim 3 wherein said tab comprises three layers of material, wherein all of said three layers are laminated to one another in said first zone and wherein all of said three layers are free to move independently with respect to one another in at least a portion of said second zone.

5. The absorbent device of claim 4 wherein said tab comprises a first outer layer and a second outer layer and an inner layer positioned between said first and said second outer layers, wherein said first outer layer and said second outer layers of said tab are independently joined to said backsheet of said absorbent device.

6. The absorbent device of claim 5 wherein said first and second outer layers of said tab are joined to said backsheet of said device on either side of said longitudinal centerline.

7. The absorbent device of claim 2 wherein said tab comprises three layers of material including a first outer layer, a second outer layer, and a middle layer, wherein said first outer layer is laminated to said middle layer in said first zone, and wherein said second outer layer is laminated to said middle layer in said first zone, and wherein said second outer layer is not laminated to another layer in said second zone thereby allowing said second layer to move independently with respect to said other layers.

8. The absorbent device of claim 7 wherein said first and second outer layers of said tab are joined to said backsheet of said device on either side of said longitudinal centerline.

9. The absorbent device of claim 2 wherein in said first zone said tab comprises three layers of material including a first outer layer, a second outer layer, and a middle layer, wherein said first outer layer is laminated to said middle layer, and wherein said second outer layer is laminated to said middle layer, said wherein in said second zone said tab comprises two layers including said first outer layer and said second outer layer, wherein said first outer layer and said second outer layer are not laminated to another layer in said second zone.

10. The absorbent device of claim 9 wherein said first and second outer layers of said tab are joined to said backsheet of said device on either side of said longitudinal centerline.

11. The absorbent device of claim 2 wherein said tab comprises two layers, wherein in said first zone said two layers are laminated to each other, and wherein in said second zone said two layers are not laminated to each other.

12. The absorbent device of claim 11 wherein said two layers of said tab are joined to said backsheet of said device on either side of said longitudinal centerline.

13. An absorbent interlabial device, said device comprising:

a liquid pervious topsheet, a liquid impervious backsheet joined to said topsheet, an absorbent core positioned between said topsheet and said backsheet, a grasping tab joined to said backsheet and depending downwardly therefrom, wherein said grasping tab comprises a first zone and a second zone; said first zone being located remote from the location of joining between said backsheet and said tab; said first zone having a first stiffness, said second zone having a second stiffness, said first stiffness being greater than said second stiffness.

* * * * *